United States Patent
Sato

(10) Patent No.: US 7,038,214 B2
(45) Date of Patent: May 2, 2006

(54) RADIOLOGICAL IMAGE PICKUP APPARATUS

(75) Inventor: Kenji Sato, Otsu (JP)

(73) Assignee: Shimadzu Corporation, Kyoto (JP)

(*) Notice: Subject to any disclaimer, the term of this patent is extended or adjusted under 35 U.S.C. 154(b) by 249 days.

(21) Appl. No.: 10/790,397

(22) Filed: Mar. 1, 2004

(65) Prior Publication Data

US 2004/0183025 A1  Sep. 23, 2004

(30) Foreign Application Priority Data

Mar. 18, 2003 (JP) .............................. 2003-073738

(51) Int. Cl.
*H01L 27/146* (2006.01)
*G01T 1/24* (2006.01)

(52) U.S. Cl. .............................. 250/370.09; 250/370.11

(58) Field of Classification Search ........... 250/370.09, 250/370.11
See application file for complete search history.

(56) References Cited

U.S. PATENT DOCUMENTS

| 5,886,353 A * | 3/1999 | Spivey et al. ........... 250/370.09 |
| 6,539,076 B1 * | 3/2003 | Shoji ......................... 378/98.8 |
| 2004/0079891 A1 * | 4/2004 | Sato et al. ............. 250/370.12 |

* cited by examiner

*Primary Examiner*—David Porta
*Assistant Examiner*—Mindy Vu
(74) *Attorney, Agent, or Firm*—Rankin, Hill, Porter & Clark LLP

(57) ABSTRACT

A light application mechanism applies light to the split electrode formation side of a semiconductor layer and an intermediate layer sensitive to radiation in an FPD, and change in the effective sensitive area does not occur, so that fluctuations in the detection sensitivity of the FPD can be circumvented. As light application is continued still after incidence of radiation stops, occurrence of residual output can also be circumvented. Further, a light strength control section controls the light application section so as to increase or decrease the strength of light applied by the light application section in response to a decrease or an increase in a gain setup value of an electric signal processing circuit, and the dark current component narrowing the dynamic range does not widely occupy the output range of the electric signal processing circuit. Consequently, the dynamic range is not largely narrowed either.

12 Claims, 6 Drawing Sheets

FIG. 3

| LED APPLICATION VOLTAGE (V) | 6.75 | 7 | 7.25 | 7.5 | 8 | 8.5 | 9 | 9.5 | 10 |
|---|---|---|---|---|---|---|---|---|---|
| ILLUMINANCE [Lux] | 6 | 10 | 22 | 57 | 320 | 760 | 1580 | 2370 | 2840 |
| DARK CURRENT INCREMENT [LSB] | 34 | 60 | 147 | 312 | 740 | 1207 | 1520 | 1780 | 1950 |
| DECREASING RATE OF DYNAMIC RANGE GAIN 30 | 0.43% | 0.75% | 1.8% | 3.9% | 9.3% | 15% | 19% | 22% | 24% |
| GAIN 20 | 0.29% | 0.50% | 1.2% | 2.6% | 6.2% | 10% | 13% | 15% | 16% |
| GAIN 10 | 0.14% | 0.25% | 0.61% | 1.3% | 3.1% | 5.0% | 6.3% | 7.4% | 8.1% |
| GAIN 5 | 0.07% | 0.13% | 0.31% | 0.65% | 1.5% | 2.5% | 3.2% | 3.7% | 4.1% |
| GAIN 2 | 0.03% | 0.05% | 0.12% | 0.26% | 0.62% | 1.0% | 1.3% | 1.5% | 1.6% |
| GAIN 1 | 0.01% | 0.03% | 0.06% | 0.13% | 0.31% | 0.50% | 0.63% | 0.74% | 0.81% |

RADIOLOGICAL IMAGE PICKUP APPARATUS

BACKGROUND OF THE INVENTION

1. Field of the Invention

The present invention relates to a radiological image pickup apparatus used in a medical, industrial, or nuclear field, etc., for amplifying an electric signal taken out from a radiation detector, which detects the spatial distribution of incident radiation, by an electric signal processing circuit and creating a radiological image by an image processing circuit based on the electric signal amplified by the electric signal processing circuit. The present invention relates in particular to an art for making it possible to circumvent fluctuations in detection sensitivity in the radiation detector for detecting the spatial distribution of incident radiation and further occurrence of residual output without narrowing the dynamic range of the electric signal processing circuit.

2. Description of the Related Art

A radiological image pickup apparatus in a related art includes a flat-panel radiation detector of direct conversion type, an electric signal processing circuit, and an image processing circuit. In the flat-panel radiation detector of direct conversion type, a common electrode for applying a bias voltage is formed on one side of a semiconductor layer sensitive to radiation (for example, X-rays) and a plurality of split electrodes are formed on an opposite side. Charges occurring in the semiconductor layer as radiation is incident are taken out as an electric signal from each of the split electrodes so that the spatial distribution of the incident radiation can be detected. The electric signal processing circuit amplifies the taken-out electric signal. The image processing circuit creates a radiological image based on the electric signal amplified by the electric signal processing circuit. Such a radiological image pickup apparatus in the related art involves problems of fluctuations in detection sensitivity of the radiation detector and occurrence of residual output in the radiation detector.

That is, the flat-panel radiation detector of direct conversion type in the related art does not have electrodes at the space between the split electrodes, from which charges moved by an electric field to the space between the split electrodes are taken out. Further, the flat-panel radiation detector of direct conversion type in the related-art has the property that charges occurring as radiation is incident is easy to be accumulated at the space between the split electrodes. Consequently, as space charges gradually accumulate in the space between the split electrodes while radiation is incident, distortion of the electric field gradually develops and the effective sensitive area changes, and therefore a phenomenon of fluctuations in the detection sensitivity occurs. In this case, after incidence of radiation stops, the space charges accumulating in the space between the split electrodes are gradually taken out from each split electrode, and therefore a phenomenon of occurrence of residual output also occurs.

Another type of a radiological image pickup apparatus in a related art includes a flat-panel radiation detector of indirect conversion type, an electric signal processing circuit, and an image processing circuit. In the flat-panel radiation detector of indirect conversion type, a plurality of semiconductor optical sensors provided by electrically splitting a semiconductor layer sensitive to light are formed on one side of a radiation-light conversion layer for converting radiation (for example, X-rays) into light. Light occurring in the radiation-light conversion layer as radiation is incident is taken out as an electric signal from each of the semiconductor optical sensors so that the spatial distribution of the incident radiation can be detected. The electric signal processing circuit amplifies the taken-out electric signal. The image processing circuit creates a radiological image based on the electric signal amplified by the electric signal processing circuit. Such a radiological image pickup apparatus in a related art also involves problems of fluctuations in detection sensitivity of the radiation detector and occurrence of residual output in the radiation detector.

SUMMARY OF THE INVENTION

It is therefore an object of the present invention to provide a radiological image pickup apparatus for making it possible to circumvent occurrence of fluctuations in detection sensitivity in radiation detector for detecting incident radiation and further occurrence of residual output without narrowing the dynamic range of an electric signal processing circuit.

To the end, according to a first aspect of the invention, there is provided a radiological image pickup apparatus comprising:

a radiation detector including a common electrode formed on one side of a semiconductor layer sensitive to radiation and a plurality of split electrodes formed on the other side of the semiconductor layer, the radiation detector taking out charges occurring in the semiconductor layer with incidence of radiation as an electric signal from each of the split electrodes and detecting the spatial distribution of the incident radiation;

an electric signal processing circuit for performing signal processing of the taken-out electric signal in response to a gain setup value and also enabling an increase or a decrease in the gain setup value;

an image processing circuit for creating a radiological image based on the electric signal subjected to signal processing by the electric signal processing circuit;

a light application section for applying light to the spilt electrode formation side of the semiconductor layer; and a light strength control section for controlling the light application section so as to increase or decrease the strength of applied light in response to a decrease or an increase in the gain setup value of the electric signal processing circuit. (Function and effect) In the first aspect of the invention, during image picking up, the light application section receiving control of the light strength control section continuously or intermittently applies light to the split electrode formation side of the semiconductor layer sensitive to radiation. At the same time, the electric signal processing circuit amplifies the electric signal taken out from the split electrodes of the radiation detector with incidence of radiation in accordance with the gain setup value. After the electric signal processing circuit amplifies the electric signal, the image processing circuit creates a radiological image simultaneously (on time) or non-simultaneously (off time) based on the electric signal corresponding to the spatial distribution of the incident radiation.

Therefore, in the first aspect of the invention, as the light application section applies light to the split electrode formation side of the semiconductor layer sensitive to radiation in the radiation detector, space charges produced by the light application accumulate in the space between the split electrodes and thus the charges occurring as radiation is incident do not accumulate and are taken out. Consequently, change in the effective sensitive area does not occur and fluctuations in the detection sensitivity of the radiation detector can be circumvented.

If light application is continued still after incidence of radiation stops, the space charges accumulating in the space between the split electrodes are not taken out and continue to accumulate and therefore occurrence of residual output can also be circumvented.

Further, as the light strength control section controls the light application section, the applied light strength increases or decreases in response to a decrease or an increase in the gain setup value of the electric signal processing circuit. That is, if the gain setup value of the electric signal processing circuit decreases, the strength of the light applied by the light application section is increased; in contrast, if the gain setup value of the electric signal processing circuit increases, the strength of the light applied by the light application section is decreased.

On the other hand, light application of the light application section carries an increase in electric signal with a dark current component added to the electric signal. The dark current component accompanying light application of the light application section increases or decreases in response to an increase or a decrease in the applied light strength; the dark current component increases as the applied light strength increases.

As a result of also amplifying the dark current component accompanying light application by the electric signal processing circuit in response to the gain setup value, the dynamic range of the electric signal processing circuit is narrowed as much as the amplified dark current component occupies the output range of the electric signal processing circuit; if the gain setup value increases, the amplification degree of the dark current component increases and therefore for the same amount of the dark current component, if the gain setup value increases, the degree of narrowing the dynamic range also increases.

In the first aspect of the invention, if the gain setup value of the electric signal processing circuit increases, the strength of light applied by the light application section is decreased and the dark current component decreases and thus the increase in the gain setup value is offset by the decrease in the dark current component and narrowing the dynamic range with the increase in the gain setup value is suppressed. In contrast, if the gain setup value of the electric signal processing circuit decreases, the strength of light applied by the light application section is increased and the dark current component increases. Then, the increase in the dark current component is offset by the decrease in the gain setup value and narrowing the dynamic range with the increase in the applied light strength is suppressed.

Therefore, widely occupying the output range of the electric signal processing circuit by the dark current component occurring with light application for circumventing fluctuations in the detection sensitivity of the radiation detector and occurrence of residual output is eliminated and therefore a situation in which the dynamic range is largely narrowed does not occur.

A second aspect of the invention is characterized by the fact that in the radiological image pickup apparatus of the first aspect of the invention, the radiation detector includes an intermediate layer having carrier selectivity, the intermediate layer being formed between the semiconductor layer and the split electrodes, and wherein the light is applied to the intermediate layer by the light application section at least during detection of radiation.

(Function and effect) According to the second aspect of the invention, although the intermediate layer having carrier selectivity is provided between the semiconductor layer and the split electrodes, similar function and effect to those in the first aspect of the invention are provided. In addition, in the presence of the intermediate layer having carrier selectivity, bend of an electric field is made to occur in the intermediate layer, so that it is made possible to lessen a dead area of the semiconductor layer, or as the light applied by the light application section reaching the semiconductor layer is suppressed, it is made possible to decrease the dark current occurrence amount in the semiconductor layer.

A third aspect of the invention is characterized by the fact that in the radiological image pickup apparatus of the first or second aspect of the invention, the split electrodes are transparent or semitransparent at the wavelength of the light applied by the light application section.

(Function and effect) According to the third aspect of the invention, the split electrodes are transparent or semitransparent, so that the applied light is applied not only to the space between the split electrodes, but also to the split electrode formation area. Thus, if radiation at a higher rate than the taking-out speed of charges is incident and charges once accumulate in the proximity of the split electrodes, they are instantly again excited by the energy of the applied light and Kinetic energy is given, so that the potential profile is not distorted and the potential in the proximity of the split electrodes does not rise. Therefore, to use a semiconductor material which needs to be used with a high bias applied, the normal operation of the circuit for taking out charges occurring in the semiconductor layer with incidence of radiation as an electric signal can also be maintained.

According to a fourth aspect of the invention, there is provided a radiological image pickup apparatus comprising:

a radiation detector including a radiation-light conversion layer for converting radiation into light and a plurality of semiconductor optical sensors formed on one side of the radiation-light conversion layer, the semiconductor optical sensors being provided by electrically splitting a semiconductor layer sensitive to light, the radiation detector taking out light occurring in the radiation-light conversion layer with incidence of radiation as an electric signal from each of the semiconductor optical sensors and detecting the spatial distribution of the incident radiation;

an electric signal processing circuit for performing signal processing of the taken-out electric signal in response to a gain setup value and also enabling an increase or a decrease in the gain setup value;

an image processing circuit for creating a radiological image based on the electric signal subjected to signal processing by the electric signal processing circuit;

a light application section for applying light to the semiconductor optical sensor formation side of the radiation-light conversion layer so that the light is not directly detected by the semiconductor optical sensors; and a light strength control section for controlling the light application section so as to increase or decrease the strength of applied light in response to a decrease or an increase in the gain setup value of the electric signal processing circuit.

(Function and effect) In the fourth aspect of the invention, during image picking up, the light application section receiving control of the light strength control section continuously or intermittently applies light to the semiconductor optical sensor formation side of the radiation-light conversion layer so that the light is not directly detected by the semiconductor optical sensors. At the same time, the electric signal processing circuit amplifies the electric signal taken out from the semiconductor optical sensors of the radiation detector with incidence of radiation in accordance with the gain setup value. Since the light application section applies light so that the light is not directly detected by the semiconductor optical sensors, the detection operation of the semiconductor optical sensors is not hindered by light application of the light application section. After the electric signal processing circuit amplifies the electric signal, the image processing circuit creates a radiological image simultaneously (on time) or non-simultaneously (off time) based on the electric signal corresponding to the spatial distribution of the incident radiation.

Therefore, in the fourth aspect of the invention, the light application section applies light to the semiconductor optical sensor formation side of the radiation-light conversion layer in the radiation detector so that the light is not directly detected by the semiconductor optical sensors, so that change in the effective sensitive area does not occur and fluctuations in the detection sensitivity of the radiation detector can be circumvented. If light application is continued still after incidence of radiation stops, the space charges accumulating in the space between the semiconductor optical sensors are not taken out and continue to accumulate and therefore occurrence of residual output can also be circumvented.

Further, as the light strength control section controls the light application section, the applied light strength increases or decreases in response to a decrease or an increase in the gain setup value of the electric signal processing circuit. That is, if the gain setup value of the electric signal processing circuit decreases, the strength of the light applied by the light application section is increased; in contrast, if the gain setup value of the electric signal processing circuit increases, the strength of the light applied by the light application section is decreased.

On the other hand, light application of the light application section carries an increase in electric signal with a dark current component added to the electric signal. The dark current component accompanying light application of the light application section increases or decreases in response to an increase or a decrease in the applied light strength; the dark current component increases as the applied light strength increases.

As a result of also amplifying the dark current component accompanying light application by the electric signal processing circuit in response to the gain setup value, the dynamic range of the electric signal processing circuit is narrowed as much as the amplified dark current component occupies the output range of the electric signal processing circuit; if the gain setup value increases, the amplification degree of the dark current component increases and therefore for the same amount of the dark current component, if the gain setup value increases, the degree of narrowing the dynamic range also increases.

In the fourth aspect of the invention, however, if the gain setup value of the electric signal processing circuit increases, the strength of light applied by the light application section is decreased and the dark current component decreases and thus the increase in the gain setup value is offset by the decrease in the dark current component and narrowing the dynamic range with the increase in the gain setup value is suppressed. In contrast, if the gain setup value of the electric signal processing circuit decreases, the strength of light applied by the light application section is increased and the dark current component increases. Then, the increase in the dark current component is offset by the decrease in the gain setup value and narrowing the dynamic range with the increase in the applied light strength is suppressed.

Therefore, widely occupying the output range of the electric signal processing circuit by the dark current component occurring with light application for circumventing fluctuations in the detection sensitivity of the radiation detector and occurrence of residual output is eliminated and therefore a situation in which the dynamic range is largely narrowed does not occur.

A fifth aspect of the invention is characterized by the fact that in the radiological image pickup apparatus of the fourth aspect of the invention, each of the semiconductor optical sensors includes an electric signal output electrode for exerting a light shield function on a side on which the light from the light application section is incident.

(Function and effect) According to the fifth aspect of the invention, the light from the light application section is shut off by the light shield function of the electric signal output electrode on the side of the semiconductor optical sensor on which the light is incident, so that the semiconductor optical sensors can be prevented from directly detecting the light from the light application section.

A sixth aspect of the invention is characterized by the fact that in the radiological image pickup apparatus of any of the first to fifth aspects of the invention, the radiation detector includes a transparent glass substrate (TFT substrate) formed with pairs of thin-film transistor switches (TFT switches) and capacitors, each pair for each spilt electrode or each semiconductor optical sensor, provided in a one-to-one correspondence with pixels of the radiological image, the transparent glass substrate being on the split electrode formation side of the semiconductor layer sensitive to radiation or the semiconductor optical sensor formation side of the radiation-light conversion layer, wherein charges of the amount responsive to the radiation incidence strength are accumulated in the capacitors via the split electrodes or via the semiconductor optical sensors with incidence of radiation and the thin-film transistor switches are switched on and off in order according to an external scan signal for reading the charges accumulated in the capacitors, whereby an electric signal is taken out.

(Function and effect) According to the sixth aspect of the invention, in the radiation detector, the light from the light application section is passed through the transparent glass substrate and is applied. At the same time, charges provided for each split electrode or for each semiconductor optical sensor and accumulated in the capacitors are taken out as an electric signal via the TFT switches. Further, leakage current of the TFT switch with light application is also added to the electric current in the amount responsive to the applied light strength as the dark current component narrowing the dynamic range. That is, the leakage current of the TFT switch increases with an increase in the applied light strength. However, the strength of the light applied by the light application section is controlled so as to increase or decrease in response to a decrease or an increase in the gain setup value of the electric signal processing circuit, so that a problem situation in which the dynamic range is narrowed because of the leakage current of the TFT switch does not occur.

That is, if the gain setup value of the electric signal processing circuit increases, the applied light strength decreases and thus the leakage current of the TFT switch decreases and the increase in the gain setup value is offset by the decrease in the leakage current, so that the dynamic range is scarcely affected. In contrast, if the gain setup value of the electric signal processing circuit decreases, the applied light strength increases and thus the leakage current of the TFT switch increases, but the increase in the leakage current is offset by the decrease in the gain setup value, so that the dynamic range is scarcely affected.

A seventh aspect of the invention is characterized by the fact that in the radiological image pickup apparatus of any of first to sixth aspects, the image processing circuit includes a correction coefficient registration section for registering an offset correction coefficient for correcting location variations in offset between electric signals and a sensitivity correction coefficient for correcting location variations in sensitivity between electric signals for each electric signal to create the radiological image, wherein the strength of the light applied by the light application section is previously classified into several steps and the offset correction coefficient and the sensitivity correction coefficient are calculated for each assumed step of the assumed light strength and are registered in the correction coefficient registration section, and wherein the image processing circuit performs offset and sensitivity variation correction processing to each electric signal based on the offset correction coefficient and the sensitivity correction coefficient already registered for the assumed step of the assumed light strength corresponding to the step of the strength of the actually applied light.

(Function and effect) According to the seventh aspect of the invention, in the image processing circuit, the offset correction coefficient for correcting location variations in offset between electric signals to create a radiological image and the sensitivity correction coefficient for correcting location variations in sensitivity between electric signals are calculated before a radiological image is created for each of the several assumed steps of the assumed light strength and are registered in the correction coefficient registration section. To create a radiological image, offset and sensitivity variation correction processing is performed based on the offset correction coefficient and the sensitivity correction coefficient already registered for the assumed strength step of the light corresponding to the step of the strength of the actually applied light, and the light strength is reflected on the variation correction processing, so that an error can be prevented from occurring in the offset and sensitivity variation corrections as light is applied by the light application section.

BRIEF DESCRIPTION OF THE DRAWINGS

FIG. 3 is a drawing showing the application voltages of the LED and the decreasing rates of the dynamic range;

DETAILED DESCRIPTION OF THE INVENTION

Referring now to the accompanying drawings, there are shown preferred embodiments of radiological image pickup apparatus of the invention (which is referred simply as image pickup apparatus whenever necessary).

First Embodiment

Figure 1:
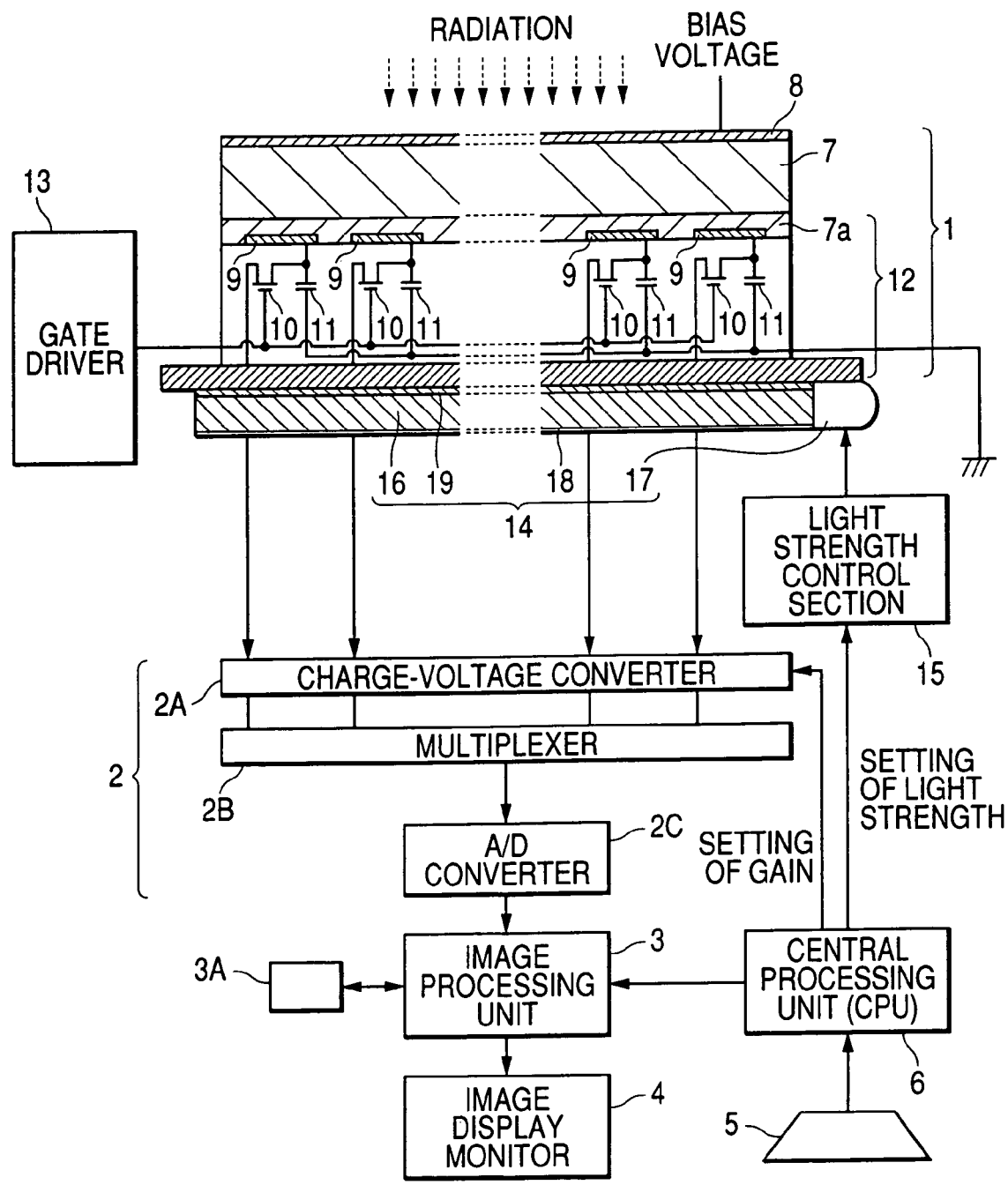
FIG. 1 is a block diagram showing the configuration of an image pickup apparatus according to a first embodiment of the invention.

FIG. 1 is a block diagram showing the configuration of an image pickup apparatus according to a first embodiment of the invention and the internal structure of a flat-panel radiation detector (radiation detector) of direct conversion type, of the image pickup apparatus.

The radiological image pickup apparatus of the first embodiment includes a flat-panel radiation detector of direct conversion type (FPD) 1, an electric signal processing circuit 2, an image processing circuit 3, an image display monitor 4, an operation section 5, and a central processing unit 6, as shown in FIG. 1. The flat-panel radiation detector of direct conversion type (FPD) 1 detects and takes out the spatial distribution of incident radiation passing through the object whose image is to be picked up (not shown) as an electric signal. The electric signal processing circuit 2 amplifies the electric signal taken out from the FPD 1. The image processing circuit 3 creates a radiological image of the object based on the electric signal amplified by the electric signal processing circuit 2. The image display monitor 4 displays the radiological image created by the image processing circuit 3. The operator performs entry operation required for picking up an image the through operation section 5. The central processing unit 6 performs necessary operations and control in response to entry operation performed through the operation section 5 and the advance state of the image pickup process. In the radiological image pickup apparatus, the radiological image corresponding to the radiological image passing through the object projected onto the FPD 1 as radiation is applied to the object is displayed on the image display monitor 4.

In the FPD 1, a common electrode 8 for applying a bias voltage is formed on one side of a semiconductor layer 7 sensitive to radiation and a two-dimensional array made up of a large number of split electrodes 9 is formed on an opposite side. A transparent glass substrate (TFT substrate) 12 is disposed on the split electrode 9 formation side of the semiconductor layer 7. The transparent glass substrate 12 is formed with pairs of thin-film transistor switches (TFT switches) 10 and capacitors 11, each pair for each spilt electrode 9, provided in a one-to-one correspondence with pixels of a radiological image.

That is, charges of the amount responsive to the radiation incidence strength are accumulated in the capacitors 11 via the split electrodes 9 as radiation is incident. A gate driver 13 switches on and off the TFT switches 10 in order according to an external scan signal for reading the charges accumulated in the capacitors 11, whereby an electric signal is taken out and the spatial distribution of the incident radiation is detected. In the embodiment, an intermediate layer 7a is placed between the semiconductor layer 7 and the split electrodes 9.

The electric signal processing circuit 2 amplifies the taken-out electric signal according to the gain value set by the central processing unit 6 (gain setup value) and can also increase or decrease the gain setup value. The gain setup value usually is set so that it is decreased if the assumed incident radiation strength increases and that it is increased if the assumed incident radiation strength decreases (namely, so that the incident radiation strength and the gain setup value are in inverse proportion).

The electric signal processing circuit 2 is made up of a charge (electric current) voltage converter 2A, a multiplexer 2B, and an A/D converter 2C, and the gain setup value is set in the charge-voltage converter 2A. In the embodiment, the radiation strength of a radiation source (not shown) is also controlled by the central processing unit 6, and the central processing unit 6 sets the gain setup value of the electric signal processing circuit 2 matching the radiation strength of the radiation source.

The radiation strength may be detected separately and the gain setup value matching the detected radiation strength may be set automatically by the central processing unit 6.

The image processing circuit 3 has a correction coefficient registration section 3A for registering an offset correction coefficient and a sensitivity correction coefficient. The offset correction coefficient is used for correcting location variations in offset between electric signals caused by location nonuniformity of the detection channel of the FPD 1 for each electric signal to create a radiological image. The sensitivity correction coefficient is used for correcting location variations in sensitivity between electric signals caused by location nonuniformity of the detection channel of the FPD 1 for each electric signal to create a radiological image. The image processing circuit 3 performs variation correction processing in the offset and the sensitivity between the electric signals based on the previously registered offset correction coefficient and sensitivity correction coefficient.

The image pickup apparatus of the embodiment includes a light application mechanism 14 and a light strength control section 15. The light application mechanism (light application section) 14 applies light to the entire surface of the split electrode 9 formation side of the semiconductor layer 7 sensitive to radiation. The light strength control section 15 controls the light application mechanism 14 so as to increase or decrease the strength of light applied by the light application mechanism 14 in response to a decrease or an increase in the gain setup value of the electric signal processing circuit 2. The light strength control section 15 controls the light application mechanism 14 so that the strength of light applied by the light application mechanism 14 increase if the gain setup value of the electric signal processing circuit 2 decreases and that the strength of light applied by the light application mechanism 14 decreases if the gain setup value increases (namely, so that the gain setup value and the light strength are in inverse proportion).

Therefore, in the embodiment, normally operation is performed so that the incident radiation strength and the gain setup value are in inverse proportion, and the gain setup value and the light strength are in inverse proportion. Consequently, the light strength control section 15 controls the light application mechanism 14 so that the strength of light applied by the light application mechanism 14 and the incident radiation strength are in direct proportion.

In the embodiment, for example, proper applied light strength is previously experimentally calculated about each gain setup value and the applied light strength is registered in association with each gain setup value. Then, at setting the gain setup value, the corresponding applied light strength is read and is set in the light strength control section 15.

Further, if the number of used radiation strengths is previously limited to several, a proper gain setup value and a proper applied light strength may be registered in association with each other for each radiation strength. Then, if the radiation strength is set, automatically the proper gain setup value and the proper applied light strength may be set.

Specifically, the light application mechanism 14 may include a light guide plate 16 made of a transparent acrylic resin disposed so as to overlap the back of the TFT substrate 12 and a light emission body 17 such as a light emitting diode or a cold-cathode tube placed on a side end face of the light guide plate 16, as shown in FIG. 1. The surface of the light guide plate 16 as the face overlapping the TFT substrate 12 may be micromachined (subjected to surface roughness treatment) and a reflection sheet 18 may be attached to the back of the light guide plate 16. Further, a dispersion sheet 19 may be placed between the TFT substrate 12 and the light guide plate 16.

In this case, light of the light emission body 17 passes through the light guide plate 16 while it is reflected on the reflection sheet 18, and is applied through the micromachined surface of the light guide plate 16 and the dispersion sheet 19, so that the light can be applied efficiently and uniformly to the split electrode 9 formation side of the semiconductor layer 7.

As another specific configuration of the light application mechanism 14, a surface light emitting diode may be put on the TFT substrate 12 with a transparent adhesive with its light emitting face directed for the TFT substrate 12. The light strength control section 15 controls the light emission amount of the light emission body 17 so that the light strength of the light emission body 17 increases or decreases in response to a decrease or an increase in the gain setup value, and also controls so as to enable the light application mechanism 14 to apply light not only during detection of radiation, but also before or after detection of radiation.

In the image pickup apparatus of the embodiment, as the light application mechanism 14 applies light to the split electrode 9 formation side of the semiconductor layer 7 and the intermediate layer 7a sensitive to radiation in the FPD 1, space charges produced by the light application accumulate in the space between the split electrodes 9 in the semiconductor layer 7 and the intermediate layer 7a, and thus the charges occurring as radiation is incident do not accumulate and are taken out. Consequently, change in the effective sensitive area does not occur and fluctuations in the detection sensitivity of the FPD 1 can be circumvented.

If light application of the light application mechanism 14 is continued still after incidence of radiation stops, the space charges accumulating in the space between the split electrodes 9 are not taken out and continue to accumulate and therefore occurrence of residual output can also be circumvented.

Subsequently, the semiconductor layer 7 and the intermediate layer 7a will be discussed more specifically.

Preferably, the wavelength of light applied to the semiconductor layer 7 and the intermediate layer 7a is a wavelength shorter than the transmittance half wavelength of the semiconductor layer 7 and the intermediate layer 7a and longer than the wavelength corresponding to band gap energy. In this case, the wavelength of applied light is shorter than the transmittance half wavelength of the used semiconductor and is longer than the wavelength corresponding to band gap energy. Thus, the applied light enters a part of the semiconductor layer 7 deeply and a dead area widens. However, the energy of the applied light is smaller than the gap band energy, and thus damage to the semiconductor layer 7 (occurrence of crystalline defect) caused by the applied light and an increase in dark current caused by charge detection by the applied light itself do not occur.

When amorphous semiconductor is used as the semiconductor layer, this mode is particularly effective because damage action to the semiconductor caused by the applied light is large in amorphous semiconductor such as amorphous selenium (a-Se).

The wavelength at which the transmittance for the intermediate layer 7a becomes 10% is about 710 nm, for example, when amorphous selenium (a-Se) is used for the intermediate layer 7a; it is about 660 nm when a thin film of antimonous sulfide ($Sb_2S_3$) is used for the intermediate layer 7a.

Preferably, the semiconductor layer 7 is any of an amorphous substance of undoped Se or an undoped Se compound, an amorphous substance of Se doped with As or Te, or Se compound doped with As or Te, an amorphous substance of Se doped with alkali metal of Na, K, Li, etc., or an Se compound doped with alkali metal of Na, K, Li, etc., an amorphous substance of Se doped with halogen of F, Cl, etc., or an Se compound doped with halogen of F, Cl, etc., or an amorphous substance of Se doped with As, Te, alkali metal of Na, K, Li, etc., and halogen of F, Cl, etc., in combination or Se compound.

Preferably, the semiconductor layer 7 is a polycrystalline substance of any of compound semiconductors CdTe, CdZnTe, $PbI_2$, $HgI_2$, TlBr, or GaAs or a polycrystalline substance of the compound semiconductor doped with halogen of F, Cl, etc.

Preferably, the wavelength of light applied to the intermediate layer 7a is shorter than the transmittance half wavelength of the intermediate layer 7a; further preferably it is shorter than the wavelength at which the transmittance for the intermediate layer 7a becomes 10%. If the intermediate layer 7a has more defects than the semiconductor layer 7 and charges accumulate in the intermediate layer 7a more easily than the semiconductor layer 7, bend of an electric field occurs only in the intermediate layer 7a. Therefore, in this case, as light is applied to the intermediate layer 7a, fluctuations in sensitivity and occurrence of residual output caused by the effect of the charges accumulating in the space between the split electrodes 9 are eliminated. As the wavelength of applied light is made shorter than the transmittance half wavelength of the intermediate layer 7a, most applied light is absorbed in the intermediate layer 7a, so that the applied light reaching the semiconductor layer 7 can be lessened. Therefore, dark current of the semiconductor layer 7 caused by the applied light can also be suppressed.

Preferably, the intermediate layer 7a is any of an amorphous substance of undoped Se or an undoped Se compound, an amorphous substance of Se doped with As or Te, or Se compound doped with As or Te, an amorphous substance of Se doped with alkali metal of Na, K, Li, etc., or an Se compound doped with alkali metal of Na, K, Li, etc., an amorphous substance of Se doped with halogen of F, Cl, etc., or an Se compound doped with halogen of F, Cl, etc., or an amorphous substance of Se doped with As, Te, alkali metal of Na, K, Li, etc., and halogen of F, Cl, etc., in combination or Se compound.

However, to cause the intermediate layer 7a to function, the material of the semiconductor layer 7 and that of the intermediate layer 7a are made different.

Preferably, the intermediate layer 7a is a polycrystalline substance of any of compound semiconductors $Sb_2S_3$, $CeO_2$, CdS, CdSe, CdTe, CdZnTe, ZnSe, ZnTe, ZnS, $PbI_2$, $HgI_2$, TlBr, or GaAs or a polycrystalline substance of the compound semiconductor doped with halogen of F, Cl, etc., or multilayer using the polycrystalline substances in combination.

If the intermediate layer 7a has a transmission limit wavelength between the transmittance half wavelength of the semiconductor layer 7 and the wavelength corresponding to the band gap energy, the filter effect can be provided for dealing with the case where it is necessary to apply light to both the semiconductor layer 7 and the intermediate layer 7a because charges accumulate in both the semiconductor layer 7 and the intermediate layer 7a. Specifically, as the material of the semiconductor layer 7 and that of the intermediate layer 7a are selected, the intermediate layer 7a is made to have the transmission limit wavelength between the transmittance half wavelength of the semiconductor layer 7 and the wavelength corresponding to the band gap energy, whereby the filter effect is produced for applying light to any desired depth. That is, the short wavelength component of wavelength components of white light is absorbed in the intermediate layer 7a and does not deeply reach the semiconductor layer 7 and most light can be made to act on the intermediate layer 7a without causing light application damage of the semiconductor layer 7 or an increase in dark current. The long wavelength component can be allowed to pass through the intermediate layer 7a to reach the semiconductor layer 7 and can be made to act thereon.

The intermediate layer 7a mentioned here is a layer having carrier selectivity and has the effect of suppressing dark current, etc. The carrier selectivity refers to the property of remarkable difference between electrons and holes of charge transfer carriers in a semiconductor in the contribution rate to the charge transfer action.

For example, substances with large contribution of electrons to the charge transfer action includes polycrystalline substances such as $CeO_2$, CdS, and CdSe of n-type semiconductors and amorphous substances of amorphous Se, etc., doped with alkali metal or As or Te for lowering contribution of holes. Substances with large contribution of holes to the charge transfer action includes polycrystalline substances such as ZnSe, ZnTe, and ZnS of p-type semiconductors and amorphous substances of amorphous Se, etc., doped with halogen for lowering contribution of electrons.

Further, there are also substances for providing large contribution of electrons or large contribution of holes depending on the film formation condition, such as $Sb_2S_3$, CdTe, CdZnTe, $PbI_2$, $HgI_2$, TlBr, or undoped amorphous Se or Se compound.

To use a film of amorphous selenium (a-Se) 1 mm thick, for example, as the semiconductor layer 7, the transmittance half wavelength is 740 mm and the wavelength corresponding to the band gap energy 2.2 eV is 560 nm. Therefore, a material having a transmission limit wavelength in the range of 560 nm to 740 nm may be used to form the intermediate layer 7a.

For example, the transmission limit wavelength of a thin film of antimonous sulfide ($Sb_2S_3$) 1 μm thick is 580 nm and thus if a thin film of antimonous sulfide 1 μm thick is formed as the intermediate layer 7a between amorphous selenium and the split electrodes 9, the short wavelength component of 580 nm or less, of applied white light is cut and the energy of the applied light becomes smaller than the band gap energy. Therefore, damage to the semiconductor layer 7 caused by the applied light and an increase in dark current are eliminated. Although the material and thickness of the intermediate layer 7a need to be selected according to the material of the semiconductor layer 7 to be used, the need for limiting the wavelength of the applied light is eliminated and the configuration involved in light application can be simplified. In other words, even if a white light source is used rather than a single-color light source as the applied light source, a radiation detector with no fluctuations in sensitivity can also be provided without causing light application damage or an increase in dark current.

The intermediate layer 7a may be placed just below the common electrode 8 rather than placed just above the split electrodes 9 as described above and further if the intermediate layer 7a is placed both just above the split electrodes 9 and just below the common electrode 8, a similar advantage to that of the configuration described above can also be provided. At the time, the materials of the intermediate layers 7a need not be the same.

Further, as the light strength control section 15 controls the light application mechanism 14, the applied light strength increases or decreases in response to a decrease or an increase in the gain setup value of the electric signal processing circuit 2, as described above.

On the other hand, light application of the light application mechanism 14 carries an increase in electric signal with a dark current component added to the electric signal. The dark current component accompanying light application of the light application mechanism 14 increases or decreases in response to an increase or a decrease in the applied light strength; the dark current component increases as the applied light strength increases.

As a result of also amplifying the dark current component accompanying light application by the electric signal processing circuit 2 in response to the gain setup value, the dynamic range of the electric signal processing circuit 2 is narrowed as much as the amplified dark current component occupies the output range of the electric signal processing circuit 2; if the gain setup value increases, the amplification degree of the dark current component increases and therefore for the same amount of the dark current component, if the gain setup value increases, the degree of narrowing the dynamic range also increases.

In the embodiment, however, if the gain setup value of the electric signal processing circuit 2 increases, the strength of light applied by the light application mechanism 14 is decreased and the dark current component decreases and thus the increase in the gain setup value is offset by the decrease in the dark current component and narrowing the dynamic range with the increase in the gain setup value is suppressed. In contrast, if the gain setup value of the electric signal processing circuit 2 decreases, the strength of light applied by the light application mechanism 14 is increased and the dark current component increases. Then, the increase in the dark current component is offset by the decrease in the gain setup value and narrowing the dynamic range with the increase in the applied light strength is suppressed.

Therefore, in the image pickup apparatus of the embodiment, widely occupying the output range of the electric signal processing circuit 2 by the dark current component occurring with light application for circumventing fluctuations in the detection sensitivity of the FPD 1 and occurrence of residual output is eliminated and therefore a situation in which the dynamic range is largely narrowed does not occur.

Subsequently, the process of finding the correspondence between the gain setup value in the electric signal processing circuit 2 and the applied light strength will be discussed specifically.

Figure 2:
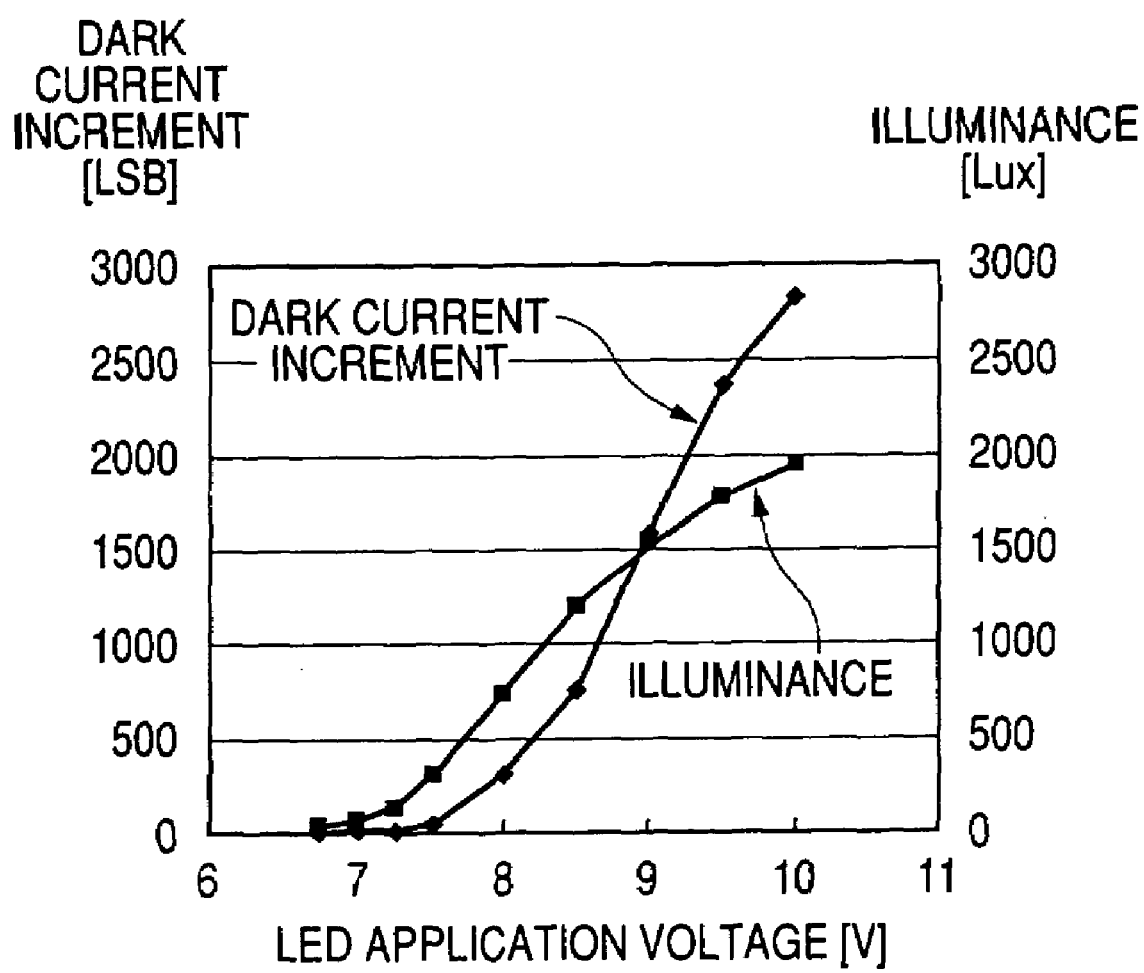
FIG. 2 is a drawing showing the relationship between application voltage of an LED of a light emission body of a light application mechanism in the first embodiment of the invention and illuminance change of the LED or dark current component produced by light application of the LED.

FIG. 2 is a graph showing change in the illuminance (light strength) of the light emitting diode (LED) of the light emission body 17 of the light application mechanism 14 in response to change in the application voltage of the LED and change in the dark current component produced by light application of the LED (dark current increment of the FPD 1). FIG. 2 assumes that the gain setup value of the electric signal processing circuit 2 is 30 and the dynamic range is 8000 LSB. When the gain setup value is changed, the dark current component produced by light application of the LED becomes [GA/30] times if the gain setup value is GA.

As shown in FIG. 2, often the illuminance of the LED does not linearly change in response to change in the application voltage of the LED, and the dark current component produced by light application of the LED corresponding to the illuminance of the LED does not correspond to the illuminance of the LED at a constant rate. Therefore, the optimum application voltage to the LED (illuminance of LED) is calculated in accordance with how much the actual dark current component produced by light application of the LED occupies the dynamic range (decreasing rate of dynamic range).

Figure 4:
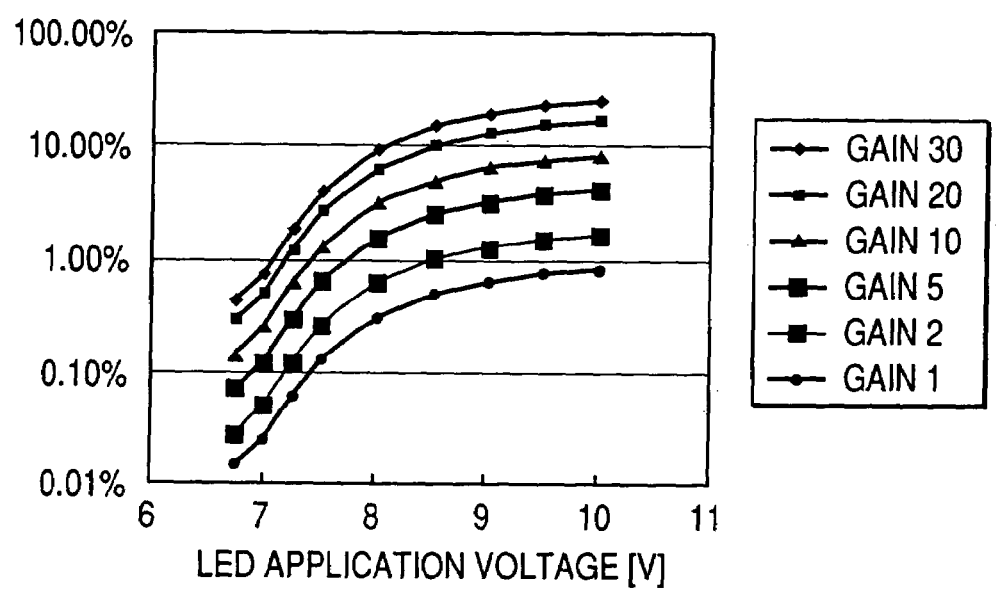
FIG. 4 is a drawing showing the correspondence between the application voltage of the LED and the decreasing rate of the dynamic range for each representative gain setup value in the electric signal processing circuit in the first embodiment of the invention.

FIG. 3 is a list of numeric data indicating the application voltages of the LED and the decreasing rates of the dynamic range corresponding thereto for each representative gain setup value. FIG. 4 is a graph to indicate the correspondence between the application voltage of the LED and the decreasing rate of the dynamic range for each representative gain setup value.

The decreasing rate of the dynamic range as a guideline varies depending on the type of radiological image of object to be picked up, etc.; for a medical radiological image requiring a wide dynamic range, it is desirable that the decreasing rate of the dynamic range should be 1% or less. Therefore, if the optimum application voltages of the LED for stepwise gain setup values in the electric signal processing circuit 2 are calculated, they are as listed in Table 1.

TABLE 1

|  | Gain | | | | | |
| --- | --- | --- | --- | --- | --- | --- |
|  | 1 | 2 | 5 | 10 | 20 | 30 |
| Optimum LED voltage [V] | 10 | 8.5 | 7.7 | 7.3 | 7.2 | 7.0 |

In the embodiment, the specific control systems of the light strength of the light emission body 17 of the light application mechanism 14 are as follows:

(Control system A) The optimum correspondences between the stepwise gain setup values and the application voltages of the LED are previously registered. To set the gain setup value in response to a stepwise increase or decrease in the gain setup value, the corresponding application voltage of the LED is read and is set in the light strength control section 15 and the LED of the light emission body 17 is lighted according to the setup application voltage. In this case, open loop control is applied.

(Control system B) The gain setup value is changed to a new one in response to a stepwise increase or decrease in the gain setup value, light of the light emission body 17 is turned on and off, and each dark current value is measured. What percentage of the dynamic range the difference between the dark current values becomes is calculated and further whether or not the calculation value is equal to or less than a predetermined decreasing rate of the dynamic range (for example, 1%) is checked. The process is repeated until the calculation value becomes equal to or less than the predetermined decreasing rate of the dynamic range (for example, 1%) while the light strength of the light emission body 17 is increased or decreased. In this case, feedback control is applied.

(Control system C) The continuous optimum correspondences between the gain setup values and the application voltages of the LED are calculated in the form of mathematical expression and are previously registered. To set the gain setup value in response to a stepwise increase or decrease in the gain setup value, the corresponding application voltage of the LED is fetched using the mathematical expression and is set in the light strength control section 15 and the LED of the light emission body 17 is lighted according to the setup application voltage. In this case, open loop control is applied.

(Control system D) The continuous optimum correspondences between the gain setup values and the application voltages of the LED are calculated in the table format as shown below and are previously registered. To set the gain setup value in response to a continuous increase or decrease in the gain setup value, the corresponding application voltage of the LED is referenced and fetched from the table and is set in the light strength control section 15 and the LED of the light emission body 17 is lighted according to the setup application voltage. Also in this case, open loop control is applied.

[Example of continuous optimum correspondences between gain setup values and application voltages of LED]

Gain setup value 1.0 LED application voltage 10.0 V
Gain setup value 1.1 LED application voltage 9.7 V
Gain setup value 1.2 LED application voltage 9.5 V
Gain setup value 1.3 LED application voltage 9.3 V (Control system E) The gain setup value is changed to a new one in response to a continuous increase or decrease in the gain setup value, light of the light emission body 17 is turned on and off, and each dark current value is measured. What percentage of the dynamic range the difference between the dark current values becomes is calculated and further whether or not the calculation value is equal to or less than a predetermined decreasing rate of the dynamic range (for example, 1%) is checked. The process is repeated until the calculation value becomes equal to or less than the predetermined decreasing rate of the dynamic range (for example, 1%) while the light strength of the light emission body 17 is increased or decreased. In this case, feedback control is applied.

In the image pickup apparatus of the embodiment, the split electrodes 9 are transparent or semitransparent at the wavelength of the light applied by the light application mechanism 14. If the split electrodes 9 are thus transparent or semitransparent, the applied light is applied not only to the space between the split electrodes 9, but also to the split electrode 9 formation area. Thus, if radiation at a higher rate than the taking-out speed of charges is incident and charges once accumulate in the proximity of the split electrodes 9, they are instantly again excited by the energy of the applied light and Kinetic energy is given, so that the potential profile is not distorted and the potential in the proximity of the split electrodes 9 does not rise. Therefore, for example, to use a-Se which needs to be used with a high bias applied, the normal operation of the TFT switches 10 can also be maintained.

In the image pickup apparatus of the embodiment, to perform variation correction processing in the offset and sensitivity between electric signals by the image processing circuit 3 based on the previously registered offset correction coefficient and sensitivity correction coefficient, the strength of the light applied by the light application mechanism 14 is reflected.

That is, the offset correction coefficient and the sensitivity correction coefficient are previously calculated by the image processing circuit 3 or the central processing unit 6 using a phantom (standard object) for registering the correction coefficients and are registered in the correction coefficient registration section 3A. In this case, the strength of the light applied by the light application mechanism 14 is previously assumed to be in several steps and the offset correction coefficient and the sensitivity correction coefficient are calculated in each assumed step of the light strength and are registered in the correction coefficient registration section 3A. The offset correction coefficient and the sensitivity correction coefficient corresponding to the strength of the light applied in actual picking up an image are read and variation correction processing is performed.

Therefore, the image processing circuit 3 performs offset and sensitivity variation correction processing so that the strength of the light applied by the light application mechanism 14 is reflected based on the offset correction coefficient and the sensitivity correction coefficient already registered in the correction coefficient registration section 3A. Consequently, an error can be prevented from occurring in the offset and sensitivity variation corrections as light is applied by the light application mechanism 14.

Next, the forming method of the image pickup apparatus of the first embodiment is as follows:

For the FPD 1 of the image pickup apparatus of the embodiment, transparent electrodes of ITO films, etc., are formed on the TFT substrate 12 as the split electrodes 9 and then a thin film of antimonous sulfide ($Sb_2S_3$) 1 μm thick is first formed as the intermediate layer 7a and next a thick film of amorphous selenium (a-Se) semiconductor 1 mm thick is formed as the semiconductor layer 7 sensitive to radiation. Then, a thin film of gold (Au) 0.1 μm thick is formed on the thick film of amorphous selenium (a-Se) semiconductor as the common electrode 8. A surface light emitting diode of green light emitting type is put on the back of the TFT substrate 12 with a transparent adhesive, whereby the light application mechanism 14 is disposed.

Next, the radiation detection operation of the image pickup apparatus of the embodiment is as follows:

As radiation, X-rays applied under the condition of tube voltage 55 kV and tube current 80 mA from an X-ray tube with an AL filter placed at a distance of 1 m from the FPD 1 were used. To apply strong X-rays, an AL filter 1 mm thick was used; to apply weak X-rays, an AL filter 26 mm thick was used. The digital output of the electric signal processing circuit 2 was set to the full range of 8000 [LSB].

The response output waveforms of the electric signal processing circuit 2 when X-rays were applied for four seconds and then stopped in operation conditions (1) to (5) listed below were measured, and the decreasing rate of the dynamic range caused by the dark current increment produced by light application, the degree of fluctuations in the detection sensitivity, and the degree of occurrence of residual output were calculated from the measurement data.

Figure 5:
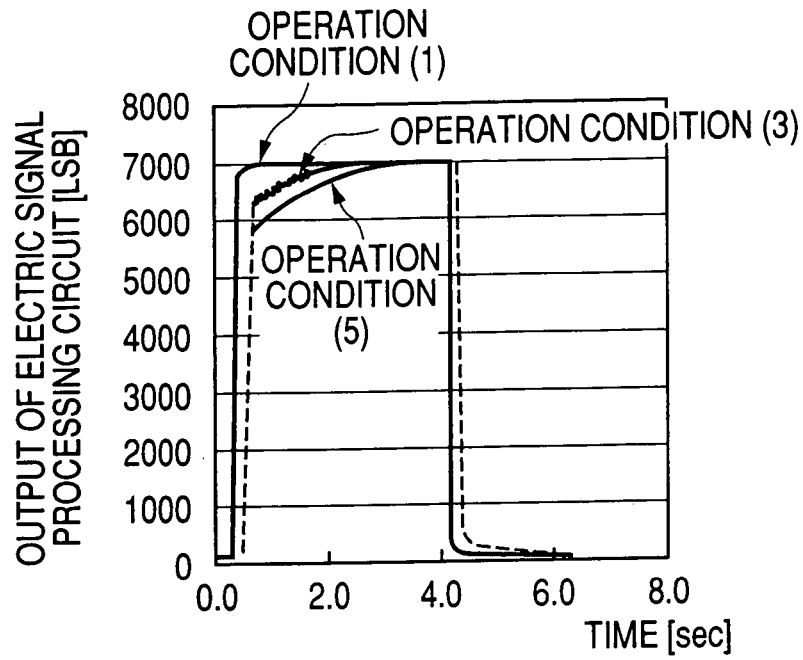
FIG. 5 is a drawing showing response output waveforms of electric signal processing circuit when strong radiation is detected in the first embodiment of the image pickup apparatus and comparative examples.
Figure 6:
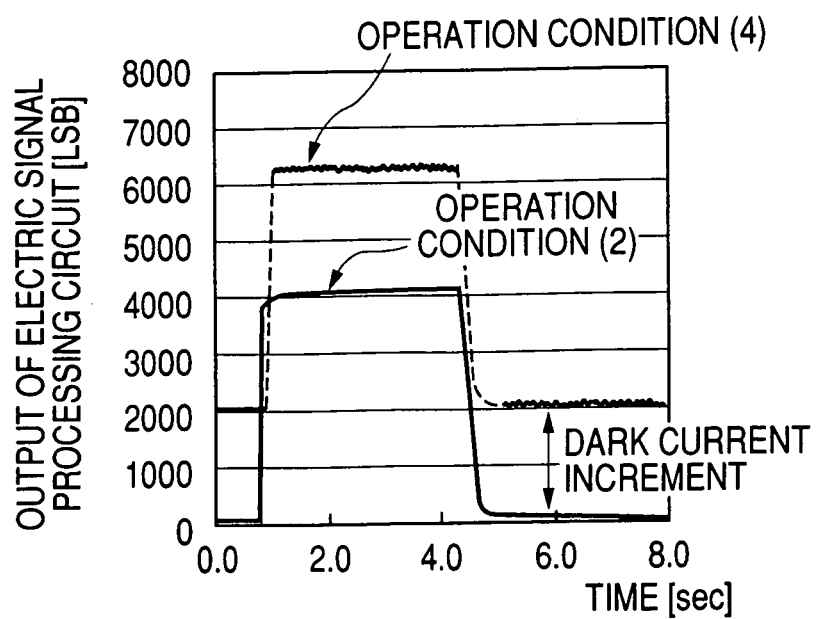
FIG. 6 is a drawing showing response output waveforms of electric signal processing circuit when weak radiation is detected in the first embodiment of the image pickup apparatus and comparative examples.

FIGS. 5 and 6 show the measurement results of the response output waveforms of the electric signal processing circuit 2, and Table 2 lists the results of the decreasing rate of the dynamic range, the degree of fluctuations in the detection sensitivity, the degree of occurrence of residual output, and the like.

Operation Condition (1)
 Application of strong X-rays
 Gain setup value of charge-voltage converter 2A: 1
 Supply voltage from light strength control section 15 to surface light emitting diode: 10 V Operation Condition (2)
 Application of weak X-rays
 Gain setup value of charge-voltage converter 2A: 30
 Supply voltage from light strength control section 15 to surface light emitting diode: 7 V Operation Condition (3)
 Application of strong X-rays
 Gain setup value of charge-voltage converter 2A: 1
 Supply voltage from light strength control section 15 to surface light emitting diode: 7 V Operation Condition (4)
 Application of weak X-rays
 Gain setup value of charge-voltage converter 2A: 30
 Supply voltage from light strength control section 15 to surface light emitting diode: 10 V Operation Condition (5)
 Application of strong X-rays
 Gain setup value of charge-voltage converter 2A: 1
 Supply voltage from light strength control section 15 to surface light emitting diode: None The operation conditions (1) and (2) are applied to the first embodiment, and the operation conditions (3) to (5) are applied to comparative examples.

TABLE 2

| | Fluctuations in detection sensitivity | Occurrence of residual output | Dark current increment | Decreasing rate of dynamic range |
|---|---|---|---|---|
| Operation condition (1) | Small | Small | 65 LSB | 0.81% |
| Operation condition (2) | Small | Small | 60 LSB | 0.75% |
| Operation condition (3) | Medium | Medium | 2 LSB | 0.03% |
| Operation condition (4) | Small | Small | 1950 LSB | 24% |
| Operation condition (5) | Large | Large | None | 0% |

Making a comparison between the embodiment and the comparative examples with respect to the data of fluctuations in detection sensitivity and occurrence of residual output in Table 2 and the response output waveforms in FIGS. 5 and 6, it is seen that when light is applied by the light application mechanism 14, controlling the light strength is effective for circumventing fluctuations in detection sensitivity and occurrence of residual output. Particularly, making a comparison between the response output waveforms in the embodiment and the comparative example in FIG. 6, it is seen that when light is applied by the light application mechanism 14, controlling is performed so that the applied light strength increases or decreases in response to a decrease or an increase in the gain setup value of the electric signal processing circuit 2, whereby a drastic decrease in the dynamic range can be circumvented.

Second Embodiment

Figure 7:
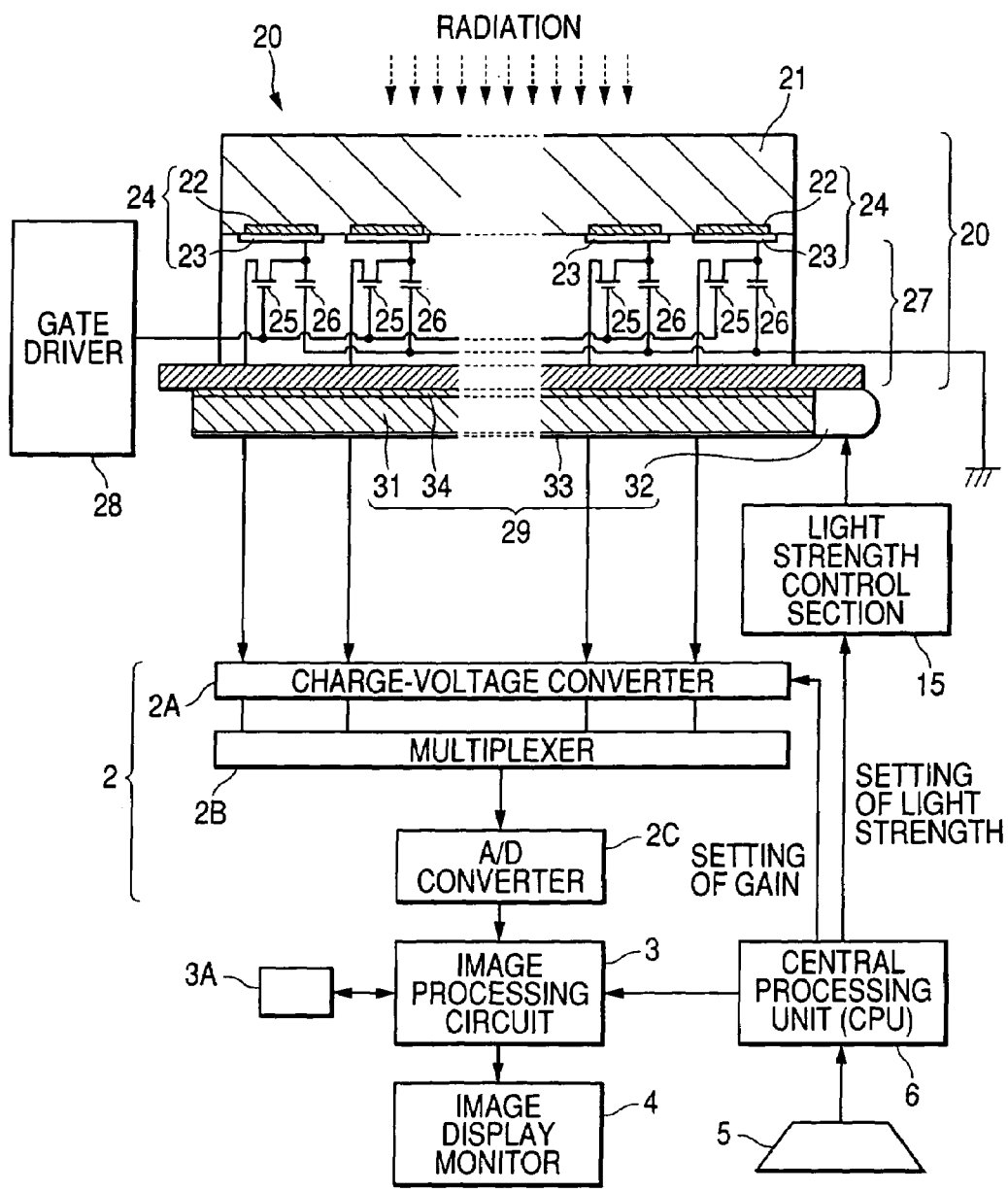
FIG. 7 is a block diagram showing the configuration of an image pickup apparatus according to a second embodiment of the invention.

FIG. 7 is a block diagram showing the configuration of an image pickup apparatus according to a second embodiment of the invention and the internal structure of a flat-panel radiation detector (radiation detector) of indirect conversion type, of the image pickup apparatus.

The image pickup apparatus of the second embodiment has the same configuration and advantages as the image pickup apparatus of the first embodiment except that it detects radiation using a flat-panel radiation detector (radiation detector) of indirect conversion type and therefore parts identical with or similar to those previously described with reference to FIG. 1 are denoted by the same reference numerals in FIG. 7 and will not be discussed again.

The radiological image pickup apparatus of the second embodiment includes a flat-panel radiation detector of indirect conversion type (FPD) 20, an electric signal processing circuit 2, an image processing circuit 3, an image display monitor 4, an operation section 5, and a central processing unit 6, as shown in FIG. 7. The flat-panel radiation detector of indirect conversion type (FPD) 20 detects and takes out the spatial distribution of incident radiation passing through the object whose image is to be picked up (not shown) in the form of an electric signal. The electric signal processing circuit 2 amplifies the electric signal taken out from the FPD 20. The image processing circuit 3 creates a radiological image of the object based on the electric signal amplified by the electric signal processing circuit 2. The image display monitor 4 displays the radiological image created by the image processing circuit 3. The operator performs entry operation required for picking up an image through the operation section 5. The central processing unit 6 performs necessary operations and control in response to entry operation performed through the operation section 5 and the advance state of the image pickup process. Therefore, the radiological image corresponding to the radiological image passing through the object projected onto the FPD 20 as radiation is applied to the object is displayed on the image display monitor 4.

In the FPD 20, a two-dimensional array made up of a large number of semiconductor optical sensors 24 is formed on one side of a radiation-light conversion layer 21 for converting radiation into light. The semiconductor optical sensors 24 are provided by electrically splitting a semiconductor layer 22 sensitive to light, each having an electric signal output electrode 23 on the back of the semiconductor layer 22. A transparent glass substrate (TFT substrate) 27 is disposed on the semiconductor optical sensor 24 formation side of the radiation-light conversion layer 21. The transparent glass substrate (TFT substrate) 27 is formed with pairs of thin-film transistor switches (TFT) 25 and capacitors 26, each pair for each semiconductor optical sensor 24, provided in a one-to-one correspondence with pixels of a radiological image.

That is, charges of the amount responsive to the radiation incidence strength are accumulated in the capacitors 26 via the semiconductor optical sensors 24 as radiation is incident. Then, a gate driver 28 switches on and off the TFT switches 25 in order according to an external scan signal for reading the charges accumulated in the capacitors 26, whereby light occurring in the radiation-light conversion layer 21 by the incident radiation is taken out as an electric signal from each of the semiconductor optical sensors 24 and the spatial distribution of the incident radiation is detected.

The image pickup apparatus of the second embodiment also includes a light application mechanism (light application section) 29 and a light strength control section 30. The light application mechanism 29 applies light to the entire surface of the semiconductor optical sensor 24 formation side of the radiation-light conversion layer 21. The light strength control section 30 controls the light application mechanism 29 so as to increase or decrease the strength of light applied by the light application mechanism 29 in response to a decrease or an increase in the gain setup value of the electric signal processing circuit 2.

The light strength control section 30 controls the light application mechanism 29 so that the strength of light applied by the light application mechanism 29 increases if the gain setup value of the electric signal processing circuit 2 decreases and that the strength of light applied by the light application mechanism 29 decreases if the gain setup value increases (namely, so that the gain setup value and the light strength are in inverse proportion).

Therefore, also in the embodiment, normally operation is performed so that the incident radiation strength and the gain setup value are in inverse proportion, and the gain setup value and the light strength are in inverse proportion. Consequently, the light strength control section 30 controls the light application mechanism 29 so that the strength of light applied by the light application mechanism 29 and the incident radiation strength are in direct proportion.

Also in the embodiment, for example, proper applied light strength is previously experimentally calculated about each gain setup value and the applied light strength is registered in association with each gain setup value and to set the gain setup value, the corresponding applied light strength is read and is set in the light strength control section 30.

Further, if the number of used radiation strengths is previously limited to several, a proper gain setup value and a proper applied light strength may be registered in association with each other for each radiation strength and if the radiation strength is set, automatically the proper gain setup value and the proper applied light strength may be set.

In the FPD 20, the electric signal output electrode 23 of each the semiconductor optical sensor 24 on the side thereof on which light from the light application mechanism 29 is incident is formed of an opaque material such as Al or Ta and has a light shield function for shielding the light from the light application mechanism 29 so that the light is not directly detected by the semiconductor optical sensor 24. The light from the light application mechanism 29 is not radiation to be detected and thus is not directly detected by the semiconductor optical sensor 24.

Specifically, the light application mechanism 29 may include a light guide plate 31 made of a transparent acrylic resin disposed so as to overlap the back of the TFT substrate 27 and a light emission body 32 such as a light emitting diode or a cold-cathode tube placed on a side end face of the light guide plate 31, as shown in FIG. 7. The surface of the light guide plate 31 as the face overlapping the TFT substrate 27 may be micromachined (subjected to surface roughness treatment) and a reflection sheet 33 may be attached to the back of the light guide plate 31. A dispersion sheet 34 may be placed between the TFT substrate 27 and the light guide plate 31.

In this case, light of the light emission body 32 passes through the light guide plate 31 while it is reflected on the reflection sheet 33, and is applied through the micromachined surface of the light guide plate 31 and the dispersion sheet 34, so that the light can be applied efficiently and uniformly to the semiconductor optical sensor 24 formation side of the radiation-light conversion layer 21.

As another specific configuration of the light application mechanism 29, a surface light emitting diode may be put on the TFT substrate 27 with a transparent adhesive with its light emitting face directed for the TFT substrate 27. The light strength control section 30 controls the light emission amount of the light emission body 32 so that the light strength of the light emission body 32 increases or decreases in response to a decrease or an increase in the gain setup value, and also controls so as to enable the light application mechanism 29 to apply light not only during detection of radiation, but also before or after detection of radiation.

In the image pickup apparatus of the embodiment, as the light application mechanism 29 applies light to the semiconductor optical sensor 24 formation side of the radiation-light conversion layer 21 for converting radiation into light in the FPD 20, space charges produced by the light application accumulate in the space between the semiconductor optical sensors 24 and thus the charges occurring as radiation is incident do not accumulate and are taken out. Consequently, change in the effective sensitive area does not occur and fluctuations in the detection sensitivity of the FPD 20 can be circumvented.

If light application of the light application mechanism 29 is continued still after incidence of radiation stops, the space charges accumulating in the space between the semiconductor optical sensors 24 are not taken out and continue to accumulate and therefore occurrence of residual output can also be circumvented.

Further, as the light strength control section 30 controls the light application mechanism 29, the applied light strength increases or decreases in response to a decrease or an increase in the gain setup value of the electric signal processing circuit 2, as described above.

On the other hand, light application of the light application mechanism 29 carries an increase in electric signal with a dark current component added to the electric signal. The dark current component accompanying light application of the light application mechanism 29 increases or decreases in response to an increase or a decrease in the applied light strength; the dark current component increases as the applied light strength increases.

As a result of also amplifying the dark current component accompanying light application by the electric signal processing circuit 2 in response to the gain setup value, the dynamic range of the electric signal processing circuit 2 is narrowed as much as the amplified dark current component occupies the output range of the electric signal processing circuit 2; if the gain setup value increases, the amplification degree of the dark current component increases and therefore for the same amount of the dark current component, if the gain setup value increases, the degree of narrowing the dynamic range also increases.

In the embodiment, however, if the gain setup value of the electric signal processing circuit 2 increases, the strength of light applied by the light application mechanism 29 is decreased and the dark current component decreases and thus the increase in the gain setup value is offset by the decrease in the dark current component and narrowing the dynamic range with the increase in the gain setup value is suppressed. In contrast, if the gain setup value of the electric signal processing circuit 2 decreases, the strength of light applied by the light application mechanism 29 is increased and the dark current component increases. Then, the increase in the dark current component is offset by the decrease in the gain setup value and narrowing the dynamic range with the increase in the applied light strength is suppressed.

Therefore, in the image pickup apparatus of the embodiment, widely occupying the output range of the electric signal processing circuit 2 by the dark current component occurring with light application for circumventing fluctuations in the detection sensitivity of the FPD 20 and occurrence of residual output is eliminated and therefore a situation in which the dynamic range is largely narrowed does not occur.

The invention is not limited to the embodiments described above and the following modifications can be made:

(1) In the second embodiment, the light shield function of each electric signal output electrode 23 in the FPD 20 prevents the semiconductor optical sensor 24 from directly detecting the light of the light application mechanism 29. However, the electric signal output electrodes 23 may be optically transparent electrodes and an opaque pattern having a light shield function may be placed for each semiconductor optical sensor 24 on the surface of the light guide plate 31, for example, on the side of the light application mechanism 29 so as to prevent the semiconductor optical sensors 24 from detecting the light of the light application mechanism 29 in the presence of the opaque pattern.

(2) A laser diode (LD) or an electroluminescent (EL) device can also be used as the light emission body of the light application mechanism in the embodiments.

(3) The image pickup apparatus of the invention can be applied not only to a medical apparatus, such as an X-ray fluoroscopic and radiographic apparatus, but also to an industrial apparatus, such as an X-ray non-destructive inspection apparatus, and the like.

As seen from the description made above, according to the first aspect of the radiological image pickup apparatus, the light application section applies light to the split electrode formation side of the semiconductor layer sensitive to radiation in the radiation detector and space charges produced by the light application accumulate in the space between the split electrodes and thus the charges occurring as radiation is incident do not accumulate and are taken out. Consequently, change in the effective sensitive area does not occur and fluctuations in the detection sensitivity of the radiation detector can be circumvented. If light application is continued still after incidence of radiation stops, the space charges accumulating in the space between the split electrodes are not taken out and continue to accumulate and therefore occurrence of residual output can also be circumvented.

If the gain setup value of the electric signal processing circuit increases, the strength of light applied by the light application section is decreased and the dark current component decreases and thus the increase in the gain setup value is offset by the decrease in the dark current component and narrowing the dynamic range with the increase in the gain setup value is suppressed. In addition, in contrast, if the gain setup value of the electric signal processing circuit decreases, the strength of light applied by the light application section is increased and the dark current component increases. Then, the increase in the dark current component is offset by the decrease in the gain setup value, narrowing the dynamic range with the increase in the applied light strength is also suppressed, and the dark current component narrowing the dynamic range does not widely occupy the output range of the electric signal processing circuit. Consequently, a situation in which the dynamic range is largely narrowed does not occur.

Further, according to the fourth aspect of the radiological image pickup apparatus, the light application section applies light to the semiconductor optical sensor formation side of the radiation-light conversion layer in the radiation detector so that the light is not directly detected by the semiconductor optical sensors, and the light of the light application section is not directly detected by the semiconductor optical sensors, so that the detection operation of the semiconductor optical sensors is not hindered. Space charges produced by the light application accumulate in the space between the semiconductor optical sensors and thus the charges occurring as radiation is incident do not accumulate and are taken out. Consequently, change in the effective sensitive area does not occur and fluctuations in the detection sensitivity of the radiation detector can be circumvented.

If light application is continued still after incidence of radiation stops, the space charges accumulating in the space between the semiconductor optical sensors are not taken out and continue to accumulate and therefore occurrence of residual output can also be circumvented.

If the gain setup value of the electric signal processing circuit increases, the strength of light applied by the light application section is decreased and the dark current component decreases and thus the increase in the gain setup value is offset by the decrease in the dark current component and narrowing the dynamic range with the increase in the gain setup value is suppressed. In addition, in contrast, if the gain setup value of the electric signal processing circuit decreases, the strength of light applied by the light application section is increased and the dark current component increases. Then, the increase in the dark current component is offset by the decrease in the gain setup value, narrowing the dynamic range with the increase in the applied light strength is also suppressed, and the dark current component narrowing the dynamic range does not widely occupy the output range of the electric signal processing circuit. Consequently, a situation in which the dynamic range is largely narrowed does not occur.

What is claimed is:

1. A radiological image pickup apparatus comprising:
    a radiation detector including a common electrode formed on one side of a semiconductor layer sensitive to radiation and a plurality of split electrodes formed on the other side of the semiconductor layer, said radiation detector taking out charges occurring in the semiconductor layer with incidence of radiation as an electric signal from each of the split electrodes and detecting the spatial distribution of the incident radiation;
    an electric signal processing circuit for performing signal processing of the taken-out electric signal in response to a gain setup value and also enabling an increase or a decrease in the gain setup value;
    an image processing circuit for creating a radiological image based on the electric signal subjected to signal processing by said electric signal processing circuit;
    a light application section for applying light to the spilt electrode formation side of the semiconductor layer; and
    a light strength control section for controlling said light application section so as to increase or decrease the strength of applied light in response to a decrease or an increase in the gain setup value of said electric signal processing circuit.

2. The radiological image pickup apparatus as claimed in claim 1, wherein said radiation detector includes an intermediate layer having carrier selectivity, the intermediate layer being formed between the semiconductor layer and the split electrodes, and wherein the light is applied to the intermediate layer by said light application section at least during detection of radiation.

3. The radiological image pickup apparatus as claimed in claim 2, wherein the split electrodes are transparent or semitransparent at the wavelength of the light applied by said light application section.

4. The radiological image pickup apparatus as claimed in claim 2, wherein said radiation detector includes a transparent glass substrate formed with pairs of thin-film transistor switches and capacitors, each pair for each spilt electrode, provided in a one-to-one correspondence with pixels of the radiological image, the transparent glass substrate being on the split electrode formation side of the semiconductor layer sensitive to radiation, wherein charges of the amount responsive to the radiation incidence strength are accumulated in the capacitors via the split electrodes with incidence of radiation and the thin-film transistor switches are switched on and off in order according to an external scan signal for reading the charges accumulated in the capacitors, whereby an electric signal is taken out.

5. The radiological image pickup apparatus as claimed in claim 2, wherein said image processing circuit includes a correction coefficient registration section for registering an offset correction coefficient for correcting location variations in offset between electric signals and a sensitivity correction coefficient for correcting location variations in sensitivity between electric signals for each electric signal to create the radiological image, wherein the strength of the light applied by said light application section is previously classified into several steps and the offset correction coefficient and the sensitivity correction coefficient are calculated for each assumed step of the assumed light strength and are registered in the correction coefficient registration section, and wherein said image processing circuit performs offset and sensitivity variation correction processing to each electric signal based on the offset correction coefficient and the sensitivity correction coefficient already registered for the assumed step of the assumed light strength corresponding to the step of the strength of the actually applied light.

6. The radiological image pickup apparatus as claimed in claim 1, wherein the split electrodes are transparent or semitransparent at the wavelength of the light applied by said light application section.

7. The radiological image pickup apparatus as claimed in claim 1, wherein said radiation detector includes a transparent glass substrate formed with pairs of thin-film transistor switches and capacitors, each pair for each spilt electrode, provided in a one-to-one correspondence with pixels of the radiological image, the transparent glass substrate being on the split electrode formation side of the semiconductor layer sensitive to radiation, wherein charges of the amount responsive to the radiation incidence strength are accumulated in the capacitors via the split electrodes with incidence of radiation and the thin-film transistor switches are switched on and off in order according to an external scan signal for reading the charges accumulated in the capacitors, whereby an electric signal is taken out.

8. The radiological image pickup apparatus as claimed in claim 1, wherein said image processing circuit includes a correction coefficient registration section for registering an offset correction coefficient for correcting location variations in offset between electric signals and a sensitivity correction coefficient for correcting location variations in sensitivity between electric signals for each electric signal to create the radiological image, wherein the strength of the light applied by said light application section is previously classified into several steps and the offset correction coefficient and the sensitivity correction coefficient are calculated for each assumed step of the assumed light strength and are registered in the correction coefficient registration section, and wherein said image processing circuit performs offset and sensitivity variation correction processing to each electric signal based on the offset correction coefficient and the sensitivity correction coefficient already registered for the assumed step of the assumed light strength corresponding to the step of the strength of the actually applied light.

9. A radiological image pickup apparatus comprising:
a radiation detector including a radiation-light conversion layer for converting radiation into light and a plurality of semiconductor optical sensors formed on one side of the radiation-light conversion layer, the semiconductor optical sensors being provided by electrically splitting a semiconductor layer sensitive to light, said radiation detector taking out light occurring in the radiation-light conversion layer with incidence of radiation as an electric signal from each of the semiconductor optical sensors and detecting the spatial distribution of the incident radiation;
an electric signal processing circuit for performing signal processing of the taken-out electric signal in response to a gain setup value and also enabling an increase or a decrease in the gain setup value;
an image processing circuit for creating a radiological image based on the electric signal subjected to signal processing by said electric signal processing circuit;
a light application section for applying light to the semiconductor optical sensor formation side of the radiation-light conversion layer so that the light is not directly detected by the semiconductor optical sensors; and
a light strength control section for controlling said light application section so as to increase or decrease the strength of applied light in response to a decrease or an increase in the gain setup value of said electric signal processing circuit.

10. The radiological image pickup apparatus as claimed in claim 9, wherein each of the semiconductor optical sensors includes an electric signal output electrode for exerting a light shield function on a side on which the light from said light application section is incident.

11. The radiological image pickup apparatus as claimed in claim 9, wherein said radiation detector includes a transparent glass substrate formed with pairs of thin-film transistor switches and capacitors, each pair for each semiconductor optical sensor, provided in a one-to-one correspondence with pixels of the radiological image, the transparent glass substrate being on the semiconductor optical sensor formation side of the radiation-light conversion layer, wherein charges of the amount responsive to the radiation incidence strength are accumulated in the capacitors via the semiconductor optical sensors with incidence of radiation and the thin-film transistor switches are switched on and off in order according to an external scan signal for reading the charges accumulated in the capacitors, whereby an electric signal is taken out.

12. The radiological image pickup apparatus as claimed in claim 9, wherein said image processing circuit includes a correction coefficient registration section for registering an offset correction coefficient for correcting location variations in offset between electric signals and a sensitivity correction coefficient for correcting location variations in sensitivity between electric signals for each electric signal to create the radiological image, wherein the strength of the light applied by said light application section is previously classified into several steps and the offset correction coefficient and the sensitivity correction coefficient are calculated for each assumed step of the assumed light strength and are registered in the correction coefficient registration section, and wherein said image processing circuit performs offset and sensitivity variation correction processing to each electric signal based on the offset correction coefficient and the sensitivity correction coefficient already registered for the assumed step of the assumed light strength corresponding to the step of the strength of the actually applied light.

* * * * *